United States Patent [19]

Dave

[11] Patent Number: 5,180,853

[45] Date of Patent: Jan. 19, 1993

US005180853A

[54] 4,4-6,6-TETRONITROADAMANTAN-2-ONE

[76] Inventor: Paritosh R. Dave, 1 Rustic Ridge Rd., A37, Little Falls, N.J. 07424

[21] Appl. No.: 878,283

[22] Filed: May 4, 1992

[51] Int. Cl.$^5$ ............... C07C 79/36; C07C 79/08; C06B 25/00
[52] U.S. Cl. .................... 568/305; 568/941; 149/88
[58] Field of Search .............. 568/941; 149/305, 88

[56] References Cited

U.S. PATENT DOCUMENTS 4,329,522  5/1982  Gilbert et al. .................. 368/941
5,105,031  4/1992  Zejac et al. ..................... 568/941

OTHER PUBLICATIONS

Davr et al., *J. Org. Chem.*, 1990, 55, 4459.

*Primary Examiner*—Edward A. Miller

[57] ABSTRACT 4,4,6,6-Tetranitroadamantan-2-one and a method of making the same.

1 Claim, No Drawings

4,4-6,6-TETRONITROADAMANTAN-2-ONE

GOVERNMENTAL INTEREST

The Government has rights in this invention pursuant to Contract Number DAAA21-89-C-0013 awarded by the U.S. Army.

The invention described herein was made under a contract with the Government and may be used and licensed by or for the Government for Governmental purposes without the payment to us of any royalties.

FIELD OF USE 4,4,6,6-Tetranitroadamantan-2-one and method of making the same. This composition is useful in an energetic composition or material such as pyrotechnics and explosives.

BACKGROUND OF THE INVENTION

Polynitropolycyclic cage molecules are central to the current efforts aimed at energetic materials to meet modern requirements for fuels, propellants and explosives. (Alster, J; Iyer, S; Sandus, O. in "The Chemistry and Physics of Energetic Materials", Bulusu S. ed., Kluwer, "The Netherlands", 1990; p. 641.) These systems are particularly attractive because strain energy incorporated in the cage combined with the accumulation of nitro groups tend to bolster energy output, while the molecular compactness produces high density materials favorably increasing the detonation velocity. For a recent review of the chemistry of polynitropolycyclic cage molecules, see Marchand, A.P. "Tetrahedron" 1988, 44,2347. Simultaneously, high crystal density materials are advantageous in volume-limited applications.

As a class of compounds, polynitroadamantanes have been of interest for more than a decade since Sollott and Gilbert first synthesized and demonstrated that the bridgehead-substituted 1,3,5,7-tetranitroadamantane exhibited very low impact sensitivity. Please see Sollott, G. P.; Gilbert, E.E. "J. Org Chem" 1980, 45,5405. Subsequently, several members of this class of compounds have been reported including 2,2-dinitro- and 2,2,6,6-tetranitroadamantane. (Archibald, T. G.; Baum, K. "J. Org Chem", 1988, 53,4645)

SUMMARY OF THE INVENTION 4,4,6,6-Tetranitroadamantan-2-one, 8, was prepared by the sequence of reactions outlined in scheme 1.

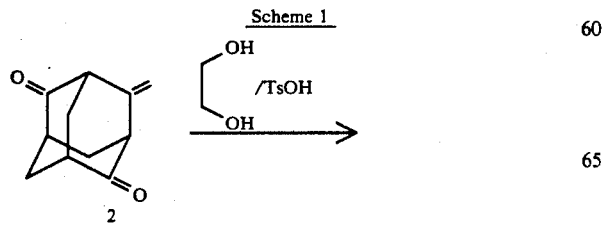

Scheme 1

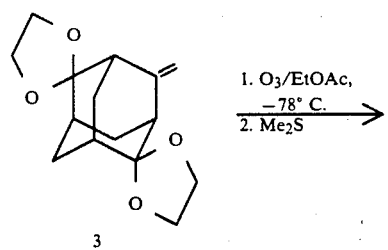

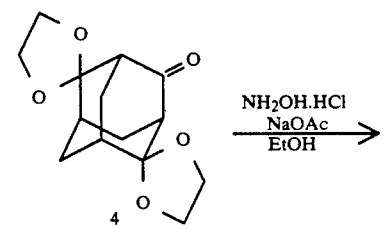

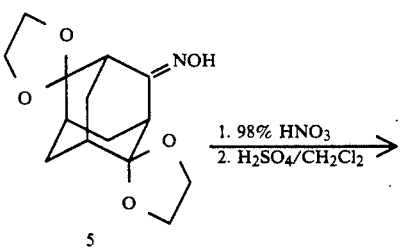

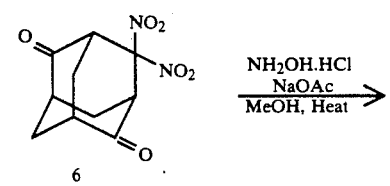

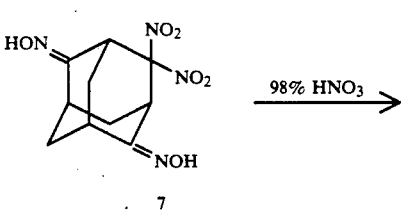

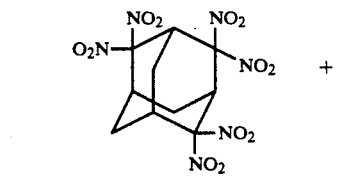

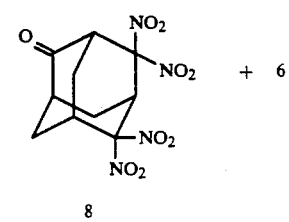

This synthetic strategy overcomes problems associated with steric crowding and takes advantage of the ease with which an oxime can be converted to the geminal dinitro function by oxidative nitration with 98% nitric acid.

The starting material for this synthesis was 4-methyleneadmantane-2,6-dione, 2, available by the treatment of bicyclo-[3.3.1]-nonane-2,6-dione (See Schaefer, J. P.; Honig, L. M. "J. Org. Chem" 1968, 33, 2655 and references therein.) with acetic anhydride and sulfuric acid. (McCabe, P. H.; Nelson, D. R.; Routledge, W. "Tetrahedron", 1977, 1749.) The carbonyl groups were protected as ethylene ketals and the exocyclic methylene unit was ozonated to yield 2,2,6,6-bis(ethylenedioxy)adamantan-4-one, 4. Compound 4 is ideally suited for the synthesis of 1 as it allows for sequential conversion of carbonyl groups that bear a 1,3, relationship as shown to be necessary in the synthesis of 2,2,4,4-tetranitroadamantane. (Dave, P. R.; Ferraro, M.; Ammon, H. L.; Choi, C. S. "J. Org. Chem" 1990, 55, 4459.) It should be noted that the corresponding bis(methylketal) has been reported (Snatzke, G.; Klein, H. "Chem. Ber." 1972, 105, 244.) Compound 4 was converted to the corresponding oxime 5, which was treated with 98% nitric acid in refluxing methylene chloride. The reaction mixture after workup showed the presence of ethylene ketal by NMR and so was treated with conc. sulfuric acid in methylene chloride to affect deketalization. The resulting mixture was purified by chromatography to afford 4,4-dinitroadamantane-2,6-dione 6 in 37% yield. Treatment of 6 with hydroxylamine hydrochloride in refluxing methanol gave the corresponding bis(oxime) 7. Treatment of 7 with 98% nitric acid in refluxing methylene chloride gave, after workup and chromatography, 2,2,4,4,6,6-hexanitroadamantane (21%) and 4,4,6,6-tetranitroadamantan-2-one (34%). A small amount of 6 was also recovered.

Thus, the synthesis of the conformationally-rigid polynitropolycylic cage molecule, 2,2,4,4,6,6-hexanitroadamantane, 1, and its precursors, 4,4,6,6-tetranitroadamantan-2-one, 8 and 4,4-dinitroadamantane-2,6-dione, 6 has been achieved.

DESCRIPTION OF THE PREFERRED EMBODIMENTS

The following section describes specific experimental procedures used for the synthesis.

2,2,6,6-bis(Ethylenedioxy)-4-methyleneadamantane, 3. A mixture of 2 (1 g, 5.7 mmol), ethylene glycol (1.4 g, 22.6 mmol) and P-Toluene Sulfonic Acid (0.1 g) in benzene was heated at reflux in a flask fitted with a dean stark tube for 4 hours. The reaction mixture was then cooled to room temperature and concentrated in vacuo. The residue was partitioned between water (100 mL) and methylene chloride (100 mL), and the layers were separated. The organic layer was washed with saturated sodium bicarbonate solution (100 mL), dried (MgSO$_4$), filtered and the filtrate was concentrated under reduced pressure. The residue was recrystallized from hexanes to give 3 as a colorless microcrystalline solid (1.3 g, 87%), mp 119°-20° C.: IR (KBr) 1650 cm$^1$ (m); $^1$H NMR (CDCl$_3$) δ1.78-2.08 (m, 8H), 2.39 (bs, 2H), 3.92-4.04 (m, 8H), 4.75 (s, 2H).

2,2,6,6-bis(Ethylenedioxy)adamantan-4-one, 4. Ozone was bubbled through a solution of 3 (0.35 g, 1.32 mmol) in ethyl acetate (50 mL) at −78° C. until the blue color of ozone persisted. The mixture was allowed to warm to room temperature and dimethyl sulfide (5 mL) was added and stirred for 30 min. The reaction mixture was then concentrated in vacuo and the residue was chromatographed on silica gel, eluting with a 1:4 mixture of acetone/hexanes to give 4 (0.15 g, 41%), mp 164°-6° C. (from acetone/hexane): IR (KBr) 1720 cm$^{-1}$ (s); $^1$H NMR (CDCl$_3$) δ1.85-2.12 (m, 2H), 2.55 (m, 2H), 3.9-4.12 (m, 8H).

2,2,6,6-bis(Ethylenedioxy)-4-oximidoadamantane, 5. To a suspension of 4 (1 g, 3.75 mmol) in absolute ethanol were added sodium acetate trihydrate (3.2 g, 23.5 mmol) and hydroxylamine hydrochloride (0.8 g, 11.5 mmol). The resulting mixture was stirred overnight at room temperature. The reaction mixture was then concentrated in vacuo and the residue was partitioned between methylene chloride (100 mL) and water (100 mL). The layers were separated and the organic layer was washed successively with saturated sodium bicarbonate solution and brine, dride (MgSO$_4$), filtered and the filtrate was concentrated under reduced pressure. The residue was recrystallized from methylene chloride/hexanes mixed solvent system to give 5 (0.9 g, 86%), mp 219°-21° C.: IR (KBr) 3260 (br, s), 1670 cm$^{-1}$ (w).

4,4-Dinitroadamantan-2,6-dione, 6. To a refluxing solution of 5 (0.9 g, 3.2 mmol) in methylene chloride (50 mL) under nitrogen was added drop wise a solution of 98% nitric acid (20 mL), urea (0.15 g, 250 mmol) and ammonium nitrate (0.15 g, 200 mmol) in methylene chlorine (20 mL). (CAUTION: 98% nitric acid should be handled carefully. Urea and ammonium nitrate should be added carefully in small portions to the nitric acid/methylene chloride solution since a slight exotherm occurs and nitrogen oxide fumes are evolved). A blue-green color appeared initially which faded as more nitric acid was added. After the addition was completed, the mixture was heated under reflux for a further 30 min. The reaction mixture was then cooled to room temperature and poured over ice (50 g). After the ice had melted the layers were separated and the organic layer was washed successively with saturated sodium bicarbonate solution (100 mL) and brine (100 mL), dried (MgSO$_4$), filtered and the filtrate was concentrated in vacuo. The residual oil was dissolved in methylene chloride (50 mL) and conc. sulfuric acid (10 mL) was added. The mixture was stirred for 3 hours at room temperature and then was poured into 100 g of ice water mixture. The layers were separated and the organic layer was washed with saturated sodium bicarbonate solution (100 mL) followed by brine (100 mL). The organic phase was dried (MgSO$_4$), filtered and the filtrate was concentrated under reduced pressure to yield a solid residue that was recrystallized from acetone/hexane mixed solvent system to give pure 6 as a colorless microcrystalline solid (0.3 g, 37%), mp 244°-46° C.: IR (KBr) 1740 (s), 1560 cm$^{-1}$ (s); $^1$H NMR (CD$_3$COCD$_3$) δ2.04-2.18 (m, 2H), 2.42-2.58 (m, 4H), 2.80 (m, 2H), 3.82 (m, 2H).

4,4-Dinitro-2,6-dioximidoadamantane, 7. To a suspension of 6 (0.3 g, 1.18 mmol) in methanol (100 mL) were added sodium acetate trihydrate (2.4 g, 17.65 mmol) and hydroxylamine hydrochloride (0.6 g, 9.30 mmol). The resulting mixture was heated under reflux for 4 hours and then stirred at room temperature overnight. The reaction mixture was then concentrated in vacuo. The residue was partitioned between methylene chloride (100 mL) and water (100 mL). The layers were separated and the organic layer was washed successively with saturated sodium bicarbonate solution (50 mL) and brine (50 mL). The organic phase was dried over MgSO$_4$, filtered and the filtrate was concentrated under reduced pressure to yield 7 (0.25 g, 76%) mp 208°–10° C. (methylene chloride/hexanes): IR (KBr) 3240 (br, s), 1660 (w), 1580 (s), 1360 cm$^{-1}$ (m).

2,2,4,4,6,6-Hexanitroadamantane, 1, and 4,4,6,6-Tetranitroadamantan-2-one, 8. To a refluxing solution of 7 (0.1 g, 0.35 mmol) in methylene chloride (25 mL) under nitrogen was added dropwise a solution of 98% nitric acid (20 mL), urea (0.15 g, 250 mmol) and ammonium nitrate (0.15 g, 200 mmol) in methylene chloride (20 mL). Initially a blue-green color appeared which faded as more nitric acid was added. After the addition was completed the mixture was further heated under reflux for 30 min. the reaction mixture was then cooled to room temperature and poured onto ice (50 g). After the ice had melted the layers were separated and the organic phase was washed successively with saturated sodium bicarbonate solution (50 mL) and brine (50 mL). The methylene chloride solution was dried (MgSO$_4$), filtered and the filtrate was concentrated in vacuo. The residue was chromatographed over silica gel using an acetone/hexane mixed solvent gradient elution (starting with 5% acetone to 30% acetone in hexane). The first fraction afforded 1 (0.03 g, 21%) as a colorless microcrystalline solid, mp 198°–200° C. (acetone/hexanes): IR (KBr) 1580 cm$^{-1}$ (s); $^1$H NMR (CDCl$_3$) δ2.1–2.4 (m, 2H), 2.65–3.15 (m, 4H), 3.35–3.54 (m, 2H), 4.76–4.80 (m, 2H).

Continued elution gave 8 as a colorless solid (0.04 g, 34%), mp 240°–41° C. (acetone/hexanes): IR (KBr) 1740 (s), 1580 cm$^{-1}$ (s); $^1$H NMR (CDCl$_3$) δ2.0–3.08, (m, 7H), 3.45–3.54 (m, 1H), 4.05–4.06 (m, 1H), 4.83–4.83 (m, 1H).

What is claimed is:

1. 4,4,6,6-Tetranitroadamantan-2-one.